US012746266B2

(12) United States Patent
Lamb

(10) Patent No.: US 12,746,266 B2
(45) Date of Patent: *Sep. 29, 2026

(54) ESSENTIAL OIL COMPOSITIONS AND APPLICATIONS UTILIZING ESSENTIAL OILS

(71) Applicant: Ralco Nutrition, Inc., Marshall, MN (US)

(72) Inventor: Richard Dale Lamb, Balaton, MN (US)

(73) Assignee: Ralco Nutrition, Inc., Marshall, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/726,831

(22) Filed: Apr. 22, 2022

(65) Prior Publication Data

US 2022/0241363 A1 Aug. 4, 2022

Related U.S. Application Data

(63) Continuation of application No. 16/352,221, filed on Mar. 13, 2019, now abandoned, which is a continuation of application No. 15/575,555, filed as application No. PCT/US2016/033271 on May 19, 2016, now Pat. No. 10,342,839.

(60) Provisional application No. 62/163,625, filed on May 19, 2015.

(51) Int. Cl.

| | |
|---|---|
| ***A61K 36/53*** | (2006.01) |
| ***A23K 10/30*** | (2016.01) |
| ***A23K 20/111*** | (2016.01) |
| ***A23K 50/30*** | (2016.01) |
| ***A23K 50/70*** | (2016.01) |
| ***A23K 50/75*** | (2016.01) |
| ***A23K 50/80*** | (2016.01) |
| ***A23L 27/10*** | (2016.01) |
| ***A23L 29/10*** | (2016.01) |
| ***A23L 29/25*** | (2016.01) |
| ***A23L 33/105*** | (2016.01) |
| ***A61K 9/00*** | (2006.01) |
| ***A61K 9/107*** | (2006.01) |
| ***A61K 9/48*** | (2006.01) |
| ***A61K 31/05*** | (2006.01) |
| ***A61K 31/11*** | (2006.01) |
| ***A61K 36/54*** | (2006.01) |

(52) U.S. Cl.

CPC .............. *A61K 36/53* (2013.01); *A23K 10/30* (2016.05); *A23K 20/111* (2016.05); *A23K 50/30* (2016.05); *A23K 50/70* (2016.05); *A23K 50/75* (2016.05); *A23K 50/80* (2016.05); *A23L 27/10* (2016.08); *A23L 29/10* (2016.08); *A23L 29/25* (2016.08); *A23L 33/105* (2016.08); *A61K 9/0014* (2013.01); *A61K 9/0053* (2013.01); *A61K 9/107* (2013.01); *A61K 9/48* (2013.01); *A61K 31/05* (2013.01); *A61K 31/11* (2013.01); *A61K 36/54* (2013.01)

(58) Field of Classification Search

None

See application file for complete search history.

(56) References Cited

U.S. PATENT DOCUMENTS

| | | | | |
|---|---|---|---|---|
| 2,479,403 | A | 8/1949 | Powers | |
| 3,628,968 | A | 12/1971 | Noznick et al. | |
| 6,106,838 | A | 8/2000 | Nitsas | |
| 6,355,684 | B1 | 3/2002 | Squires | |
| 6,399,356 | B1 | 6/2002 | Benhardt et al. | |
| 6,541,042 | B1 | 4/2003 | Frater-Schroder et al. | |
| 6,680,074 | B1 | 1/2004 | Morice | |
| 6,703,056 | B2 | 3/2004 | Mehansho et al. | |
| 7,048,953 | B2 | 5/2006 | Vail, III et al. | |
| 7,429,396 | B2 | 9/2008 | D'Amelio, Sr. et al. | |
| 8,158,687 | B2 | 4/2012 | Yaghmur et al. | |
| 8,507,734 | B2 | 8/2013 | Chen et al. | |
| 9,949,490 | B2 * | 4/2018 | Lamb | C05D 9/02 |

(Continued)

FOREIGN PATENT DOCUMENTS

| | | | | |
|---|---|---|---|---|
| CA | 2695157 | A1 | 2/2009 | |
| DE | 202004021155 | U1 * | 2/2007 | A23K 20/174 |

(Continued)

OTHER PUBLICATIONS

"First Examination Report for AU application No. 2021204342, mailed on Oct. 24, 2022", 2 Pages.

(Continued)

*Primary Examiner* — Susan T Tran

(74) *Attorney, Agent, or Firm* — Merchant & Gould, P.C.

(57) ABSTRACT

Embodiments of the present disclosure describe compositions for increasing the health and feed efficiency of an animal comprising one or more essential oils, wherein the one or more essential oils include at least thyme essential oil and cinnamon essential oil; and an emulsifier, wherein the one or more essential oils are present as an emulsion and the average particle size of the one or more essential oils in the emulsion is about 25 microns or less. Embodiments of the present disclosure describe compositions for increasing the health and feed efficiency of an animal comprising one or more essential oils, wherein the one or more essential oils include at least thyme essential oil and cinnamaldehyde; and an emulsifier, wherein the one or more essential oils are present as an emulsion and the average particle size of the one or more essential oils in the emulsion is about 25 microns or less.

14 Claims, 4 Drawing Sheets

(56) References Cited

U.S. PATENT DOCUMENTS

| | | | | |
|---|---|---|---|---|
| 10,342,839 | B2 * | 7/2019 | Lamb | A23K 50/70 |
| 10,512,664 | B2 | 12/2019 | Lamb et al. | |
| 12,491,225 | B2 | 12/2025 | Lamb et al. | |
| 2001/0000468 | A1 * | 4/2001 | Mak | C08B 37/006 424/47 |
| 2002/0155194 | A1 | 10/2002 | Mehansho et al. | |
| 2005/0014827 | A1 | 1/2005 | Schur | |
| 2006/0018867 | A1 | 1/2006 | Kawasaki et al. | |
| 2007/0036831 | A1 | 2/2007 | Baker | |
| 2007/0154504 | A1 | 7/2007 | Coats et al. | |
| 2008/0125321 | A1 | 5/2008 | Rohlfsen | |
| 2009/0004308 | A1 | 1/2009 | Frehner et al. | |
| 2009/0186096 | A1 * | 7/2009 | Kritzman | A61K 36/13 514/345 |
| 2009/0202643 | A1 | 8/2009 | Yamada et al. | |
| 2011/0076306 | A1 | 3/2011 | Rodriguez et al. | |
| 2011/0150995 | A1 | 6/2011 | Joshi | |
| 2012/0083530 | A1 * | 4/2012 | Mai | A61P 29/00 514/560 |
| 2012/0093952 | A1 | 4/2012 | Frehner et al. | |
| 2012/0219602 | A1 | 8/2012 | Flack et al. | |
| 2013/0004617 | A1 | 1/2013 | Zhang et al. | |
| 2013/0131121 | A1 | 5/2013 | Tsuchida et al. | |
| 2013/0252909 | A1 | 9/2013 | Kraus et al. | |
| 2013/0287919 | A1 * | 10/2013 | Philippov | A23L 3/3463 426/541 |
| 2014/0030203 | A1 | 1/2014 | Dombeck | |
| 2014/0045692 | A1 | 2/2014 | Rossines et al. | |
| 2015/0004262 | A1 | 1/2015 | Al-Yaqout et al. | |
| 2015/0299058 | A1 | 10/2015 | Lamb et al. | |
| 2016/0106799 | A1 | 4/2016 | Zhang et al. | |
| 2016/0206654 | A1 | 7/2016 | Sandberg | |
| 2019/0209637 | A1 | 7/2019 | Lamb | |
| 2020/0197470 | A1 | 6/2020 | Lamb et al. | |
| 2022/0016194 | A1 | 1/2022 | Lamb et al. | |
| 2024/0139271 | A1 | 5/2024 | Lamb et al. | |

FOREIGN PATENT DOCUMENTS

| | | | | |
|---|---|---|---|---|
| EP | 3297452 | A1 | 3/2018 | |
| GB | 2503235 | A | 12/2013 | |
| JP | 56-15831 | A | 2/1981 | |
| MX | 2016013621 | A | 6/2017 | |
| WO | 98/42188 | A1 | 10/1998 | |
| WO | 99/08536 | A1 | 2/1999 | |
| WO | 200221930 | A1 | 3/2002 | |
| WO | 03/018042 | A1 | 3/2003 | |
| WO | 2004091307 | A1 | 10/2004 | |
| WO | 2007/094000 | A2 | 8/2007 | |
| WO | 2008155536 | A1 | 12/2008 | |
| WO | 2012/076717 | A1 | 6/2012 | |
| WO | WO-2012072488 | A1 * | 6/2012 | A01N 25/04 |
| WO | WO-2013056078 | A2 * | 4/2013 | A23L 1/0032 |
| WO | 2014/135650 | A1 | 9/2014 | |
| WO | WO-2014151449 | A1 * | 9/2014 | A01N 25/04 |
| WO | 2015032922 | A1 | 3/2015 | |
| WO | WO-2015047413 | A1 * | 4/2015 | A23K 20/10 |
| WO | 2015161269 | A1 | 10/2015 | |
| WO | 2016004326 | A1 | 1/2016 | |
| WO | 2016014699 | A1 | 1/2016 | |
| WO | 2016187422 | A1 | 11/2016 | |

OTHER PUBLICATIONS

Michiels, et al., "In vitro dose-response of carvacrol, thymol, eugenol and trans-cinnamaldehyde and interaction of combinations for the antimicrobial activity against the pig gut flora", vol. 109, No. 1-3, doi:10.1016/J.LIVSCI.2007.01.132, ISSN 1871-1413, Apr. 29, 2007, pp. 157-160.

Si, et al., "In vitro assessment of antimicrobial activity of carvacrol, thymol and cinnamaldehyde towards *Salmonella* serotype Typhimurium DT104: effects if pig diets and emulsification in hydrocolloids", vol. 101, No. 6, doi:10.1111/J.13652672.2006.03045.X, Dec. 1, 2006, pp. 1282-1291.

Astani et al., "Comparative Study on the Antiviral Activity of Selected Monoterpenes Derived from Essential Oils," Phytotherapy Research, vol. 24, pp. 673-679 (2010).

Bassole et al., "Essential oils in Combination and Their antimicrobial Properties", Molecules, vol. 17, pp. 3989-4006 (2012).

Bohme et al., "Antibacterial, Antiviral and Antifungal Activity of Essential Oils: Mechanisms and Applications," Antimicrobial Compounds: Current Strategies and New Alternatives, Springer-Verlag Berlin, Heidelberg, Chapter 3, pp. 51-81 (2014).

Buzzini et al., "Antimicrobial and Antiviral Activity of Hydrolysable Tannins," Mini-Reviews in Medicinal Chemistry, vol. 8, No. 12, pp. 1179-1187 (2008).

Dabbah et al., Antimicrobial Action of Some Citrus Fruit Oils on Selected Food-Borne Bacteria, Applied Microbiology, vol. 19, No. 1, pp. 27-31 (Jan. 1970).

Dion et al., "Does larch arabinogalactan enhance immune function? A review of mechanistic and clinical trials," Nutrition and Metabolism, 13:28, DOI 10.1186/s12986-016-0086-x (2016).

Ghosh et al. "Cinnamon Oil Nanoemulsion Formulation by Ultrasonic Emulsification: Investigation of Its Bactericidal Activity," Journal of Nanoscience and Nanotechnology, vol. 13, No. 1, pp. 114-122 (2013).

Gutierrez et al., "The antimicrobial efficacy of plant essential oil combinations and interactions with food ingredients," International Journal of Food Microbiology, vol. 124, No. 1, pp. 91-97 (2008).

Hayashi et al., "Inhibitory effect of cinnamaldehyde, derived from Cinnamomi cortex, on the growth of influenza A/PR/8 virus in vitro and in vivo," Antiviral Research, vol. 74, pp. 1-8 (2007).

Hoffman-Pennesi, "Antioxidant, Antibacterial, and Antiviral Effects of Two Essential Oils, Their Components, and Caffeic Acid for use as Feed Additives in Poultry," Master's Thesis, University of Delaware 2010. (Year: 2010).

Hognadottir, "Identification of aroma active compounds in orange essence oil using gas chromatography—olfactometry and gas chromatography—mass spectrometry," Journal of Chromatography A, vol. 998, pp. 201-211 (2003).

Hyldgaard et al., "Essential oils in food preservation: mode of action, synergies, and interactions with food matrix :: omponents", Frontiers in Microbiology, Jan. 2012, vol. 3, Article 12, pp. 1-24 (Jan. 25, 2012).

Koch, "Inhibitory effect of essential oils against herpes simplex virus type 2," Phytomedicine, vol. 15, Issues 1-2, pp. 71-78 (2008).

Liu et al., "The Antiadenovirus Activities of Cinnamaldehyde In Vitro," Laboratory Medicine, vol. 40, No. 11, pp. 669-674 (2009).

Maniki et al. "Chemical Composition, Antioxidant, and Antibiofilm Properties of Essential Oil from Thymus capitatus Plants Organically Cultured on the Greek Island of Lemnos," Molecules, 28(3), 1154, https://doi.org/10.3390/molecules28031154, 18 pages (2023).

Meneses et al., "Inhibitory effect of essential oils obtained from plants grown in Colombia on yellow fever virus replication in vitro," Annnals of Cliical Microbilogy and Antimicrobials, doi: 10.1186/1476-0711-8-8, vol. 8, Article No. 8, 6 pages (2009).

Osman et al., "Characterization of Commercial Samples of Gum Arabic," J. Agric. food Chem., vol. 41, pp. 71-77 (1993).

PCT/US2015/041592, "International Search Report and Written Opinion", 9 pages (Oct. 29, 2015).

Reichling et al., "Essential Oils of Aromatic Plants with Antibacterial, Antifungal, Antiviral, and Cytotoxic Properties—an Overview," Forsch Komplementmed, vol. 16, No. 2, pp. 79-90 (2009).

Renard et al., "Structure of arabinogalactan-protein from Acacia gum: From porous ellipsoids to supramolecular architectures," Carbohydrate Polymers, vol. 90, pp. 322-332 (2012).

Search Report and Written Opinion for PCT/US2016/033271 mailed on Jul. 15, 2016.

Smith-Palmer et al., "Antimicrobial properties of plant essential oils and essences against five important food-borne pathogens," Letters in Applied Microbiology, vol. 26, pp. 118-122 (1998).

Theisen et al., "Tannins from Hamamelis virginiana Bark Extract: Characterization and Improvement of the Antiviral Efficacy against Influenza A Virus and Human Papillomavirus," PLoS ONE 9(1): e88062. doi: 10.1371/journal.pone.0088062.

(56) References Cited

OTHER PUBLICATIONS

Van Aken, "Polysaccharides in Food Emulsions," Chapter 15 of Food Polysaccharides and Their Applications, Second Edition, edited by Alistair M. Stephen, Glyn O. Phillips, and Peter A Williams, Boca Raton, FL: Taylor and Francis Group, pp. 521-539 (2006).
Vimalanathan et al., "Anti-Influenza Virus Activities of Commercial Oregano oils and their Carriers," Journal of Applied Pharmaceutical Science, vol. 2, Issue 7, pp. 214-218 (2012).
Yorgancioglu et al., "Production of cosmetic purpose collagen containing antimicrobial emulsion with certain essential oils," Industrial Crops and Products, vol. 44, pp. 378-382 (2013).
Kalemba et al., "Antibacterial and Antifungal Properties of Essential Oils," Current Medicinal Chemistry, vol. 10, pp. 813-829 (2003).

* cited by examiner

ESSENTIAL OIL COMPOSITIONS AND APPLICATIONS UTILIZING ESSENTIAL OILS

CROSS REFERENCE TO RELATED APPLICATION

This application is a continuation of U.S. application Ser. No. 16/352,221, filed Mar. 13, 2019, which is a continuation of U.S. application Ser. No. 15/575,555, filed on Nov. 20, 2017, now U.S. Pat. No. 10,342,839, which is a National Stage Application of International Application No. PCT/US2016/033271, filed on May 19, 2016, which claims priority to U.S. Provisional Application No. 62/163,625, filed May 19, 2015, which applications are incorporated by reference in their entirety.

BACKGROUND

Efficient rearing of livestock and other animals is dependent upon ensuring high growth rates, feed intake, productivity, and reproductive success. Some of the greatest threats to animal growth and productivity include bacterial and fungal infections, and oxidative stress. Hormones and antibiotics are commonly used as productivity and growth promoters in animals. For example, antibiotics, such as coccidiostats, are often administered regularly in subtherapeutic doses to promote animal health and growth. However, these approaches have garnered significant outcry from scientific and social communities over the past decade.

Subtherapeutic antibiotics have been linked to pathogenic antibiotic resistance in animals, and their use as animal feed additives and growth promoters are banned in many countries. Similarly, animal hormonal supplements have been linked to detrimental side effects in animals as well as public health concerns for humans. Further, the need for alternatives to subtherapeutic antibiotics and hormonal growth promoters is readily recognized by the significant economic incentive to market animal products as “natural”, “organic”, “hormone-free” and “antibiotic-free”.

Essential oils such as oregano, thyme, and cinnamon have been disclosed in the art primarily as flavoring or odorizing agents. Essential oils have in some instances been disclosed as pharmaceuticals for medical and veterinary uses, yet the efficacy and compatibility of multi-essential oil blends are unpredictable and often undesirable. For example, U.S. Pat. No. 6,106,838 teaches that essential oils of thyme and oregano exhibit antagonist effects when combined for pharmaceutical uses.

SUMMARY

In general, embodiments of the present invention provide animal treatment compositions, and methods of making and using such products and compositions. The use of these products and compositions can act as nutritional and feed supplements to enhance the health and feed efficiency of animals.

Embodiments of the present disclosure describe compositions for increasing the health and feed efficiency of an animal comprising one or more essential oils, wherein the one or more essential oils include at least thyme essential oil and cinnamon essential oil; and an emulsifier, wherein the one or more essential oils are present as an emulsion and the average particle size of the one or more essential oils in the emulsion is about 25 microns or less.

Embodiments of the present disclosure describe compositions for increasing the health and feed efficiency of an animal comprising one or more essential oils, wherein the one or more essential oils include at least thyme essential oil and cinnamaldehyde; and an emulsifier, wherein the one or more essential oils are present as an emulsion and the average particle size of the one or more essential oils in the emulsion is about 25 microns or less.

Embodiments of the present disclosure describe methods of enhancing the health and feed efficiency of an animal comprising administering an essential oil composition to an animal, wherein the essential oil composition includes one or more essential oils and an emulsifier, wherein the one or more essential oils include at least thyme essential oil and cinnamon essential oil, wherein the one or more essential oils are present as an emulsion and the average particle size of the one or more essential oils in the emulsion is about 25 microns or less.

DETAILED DESCRIPTION

Figure 1:
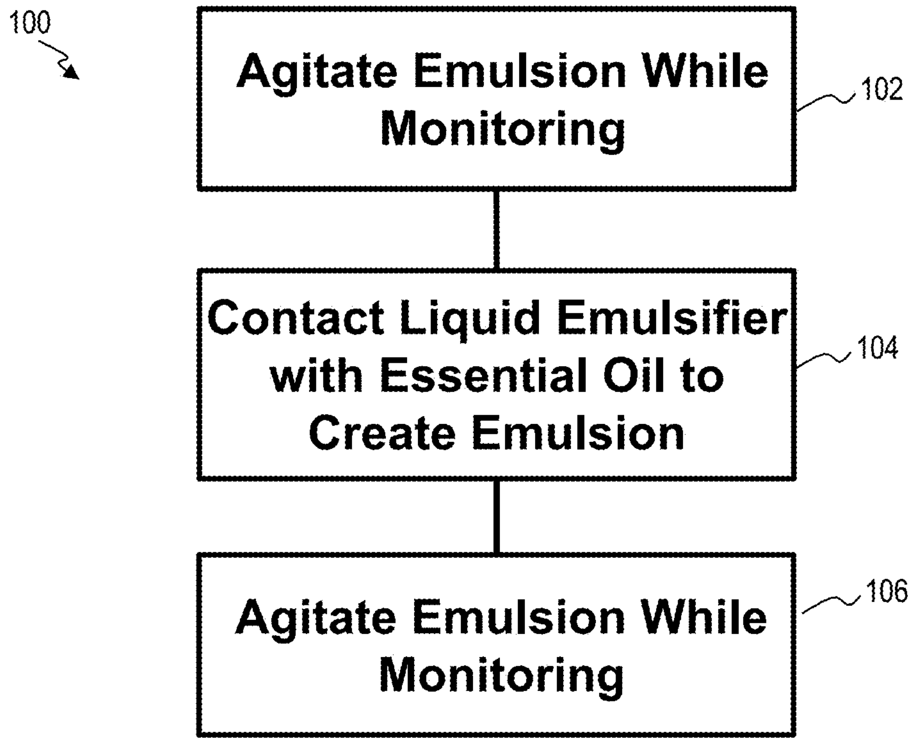
FIG. 1 illustrates a block flow diagram of a method of making an essential oil dispersion, according to one or more embodiments.

This disclosure relates to essential oil compositions for use as animal supplement and feed compositions containing essential oils from oregano, thyme and cinnamon. These essential oil compositions enhance the feed efficiency and health of animals, and additionally obviate the need for products such as hormonal and/or subtherapeutic antibiotic growth promoters.

As used herein, the recited terms have the following meanings. All other terms and phrases used in this specification have their ordinary meanings as one of skill in the art would understand after review of this disclosure.

As used herein, “plants” and “plant derivatives” can refer to any portion of a growing plant, including the roots, stems, stalks, leaves, branches, seeds, flowers, fruits, and the like. For example, cinnamon essential oil can be derived from the leaves or bark of a cinnamon plant.

As used herein, the term “essential oils” refers to aromatic, volatile liquids extracted from plant material. Essential oils are often concentrated hydrophobic liquids containing volatile aroma compounds. Essential oil chemical constituents can fall within general classes, such as terpenes (e.g., p-Cymene, limonene, sabinene, a-pinene, y-terpinene, b-caryophyllene), terpenoids (e.g., citronellal, thymol, carvacrol, carvone, borneol) and phenylpropanoids (e.g., cinnamaldehyde, eugenol, vanillin, safrole). Essential oils can be natural (i.e., derived from plants), or synthetic.

As used herein "cinnamon essential oil" refers to one or more of natural cinnamon oil (i.e., essential oil derived from plants in the *Cinnamomum* genus), or synthetic cinnamon oil. Synthetic cinnamon essential oil can comprise synthetic cinnamaldehyde. Synthetic cinnamon essential oil can further comprise one or more major constituents of natural cinnamon essential oil. A major constituent is one which comprises at least 1 wt. %, at least 2.5 wt. %, or at least 5 wt. % of a natural essential oil assay.

As used herein "thyme essential oil" refers to one or more of natural thyme oil (i.e., essential oil derived from plants in the *Thymus* genus), or synthetic thyme oil. Synthetic thyme essential oil can comprise synthetic thymol. Synthetic thyme essential oil can further comprise one or more major constituents of natural thyme essential oil.

As used herein "oregano essential oil" refers to refers to one or more of natural oregano oil (i.e., essential oil derived from plants in the *Origanum* genus), or synthetic oregano oil. Synthetic oregano essential oil can comprise synthetic carvacrol. Synthetic oregano essential oil can further comprise one or more major constituents of natural oregano essential oil.

As used herein, the term "emulsion" refers to a fine dispersion of droplets of one liquid in which the liquid is not substantially soluble or miscible. An essential oil may be emulsified or substantially emulsified within an aqueous carrier, for example.

As used herein, the term "emulsifier" refers to a substance that stabilizes an emulsion. The emulsifier can utilize physical properties, chemical properties, or utilize both physical and chemical properties to interact with one or more substances of an emulsion. Tannic acid is an example of an emulsifier for essential oils and water.

As used herein, the term "tannin compound" refers to a polyphenolic biomolecule including at least twelve hydroxyl groups and at least five phenyl groups. Tannin compounds include compounds utilizing gallic acid, flavone and phloroglucinol as base units. Tannic acid ($C_{76}H_{52}O_{46}$) is one form of a tannin compound. Tannic acid can include quercitannic acid and gallotannic acid, for example.

As used herein, "carrier" refers to a substance that physically binds or combines, or chemically binds or combines, with a target or active substance to facilitate the use, storage, or application of the target or active substance. Carriers are often inert materials, but can also include non-inert materials when compatible with the target or active substances. Examples of carriers include, but are not limited to, water for compositions that benefit from a liquid carrier, or diatomaceous earth for compositions that benefit from a solid carrier.

As used herein, "enzymes" refers to one or more biological molecules capable of breaking down cellulosic material. Enzymes include starch, proteins, non-starch polysaccharides, both soluble and insoluble, lignins and those biological molecules that facilitate chemical reactions within plants and animals.

As used herein, "animal" refers to all living organisms including humans.

As used herein, "poultry" refers to birds of the order Galliformes including ordinary domestic fowl or chicken (*Gallus domesticus*), turkeys (*Meleagris*), pheasants (*Phasianus*), partridges (*Perdix*), grouse (*Lagopus*), guinea fowl (*Numida*) peacocks (*Pavo*), and also birds of the order Anseriformes such as ducks (*Anas*) and geese (*Anser*).

In this disclosure, the novel utility of multi-essential oil compositions will be demonstrated. This disclosure relates to compositions including essential oils for enhancing feed efficiency and health of a subject. In many embodiments, subjects include animals. Enhancing feed efficiency can increase the growth rate, weight, weight gain rate, and nutrition of an animal. Enhanced health generally includes one or more of reduced or eliminated microbial infection, reduced or eliminated oxidative stress, reduced or eliminated infection or death during transport, reduced or eliminated microbial infection, increased body weight, enhanced egg characteristics increased rate of weight gain, increased growth rate, reduced or eliminated birth mortality, increased or improved body score conditions, increased reproductive success, and increased gut health maturation.

Reproductive success refers to general health outcomes and effects of both the mother and the young. Maturation of the gut can include developing beneficial indigenous microflora within the gut. Enhanced egg characteristics can include one or more of increased egg size uniformity, increased egg shape uniformity, increased egg size, increased numbers of eggs laid per clutch, increased egg clutch frequency, increased egg hatchability, increased egg shell thickness, increased egg shell thickness uniformity. Enhanced egg characteristics can be achieved in all oviparous and ovuliparous animals, which include fish, amphibians, reptiles, birds, monotremes, insects, molluscs, and arachnids. As used herein, "clutch" refers to a single period or instance of egg laying for all oviparous and ovuliparous animals.

Enhanced health can include various benefits specific to a certain class of animals For example, enhanced health in poultry can include increased growth rate, feed efficiency, egg shell thickness and mortality rate Enhanced health in dairy cows, or other milk-producing animals such as camels, goats, and sheep, can include increased milk production. In swine, for example, enhanced health can include a reduction or elimination of wasting diseases and mulberry heart.

Oxidative stress can include oxidative damage of tissues and cellular components, and is known to be a primary or secondary cause of many animal diseases. Oxidative stress can be measured by the concentration of reactive oxygen species (ROS) in a subject. In general, the five most damaging ROS include peroxyl radicals (e.g., R—$O_2$; oxidation of polyunsaturated fatty acids by $OH^-$), hydroxyl radicals ($OH^-$), peroxynitrite (e.g., $ONO^{2-}$; $H_2O_2$+$NO^{2-}$), superoxide anion (e.g., $O^{2-}$), and singlet oxygen ($1O_2$). In animals, a variety of ROS are naturally produced through metabolic processes and by certain leukocyte populations during immune responses against disease. For example, the superoxide anion is produced by ATP synthesis. Environmental sources such as UV radiation can also increase ROS prevalence in an animal. For example, a grazing animal may have a higher singlet oxygen concentration from increased exposure to sunlight. ROS can damage cells through direct oxidation, or indirectly by inciting chemical and/or biological chain reactions which damage cells.

Antioxidants are molecules which are capable of slowing or preventing the oxidation of other molecules, and can be hydrophilic or lipophilic. Hydrophilic antioxidants can react with ROS in cell cytoplasm and blood plasma, for example. Lipophilic antioxidants can protect cell membranes from lipid peroxidation, for example. Host animals naturally produce antioxidants (e.g., glutathione, superoxide dismutase, catalase, peroxidases, uric acid, vitamin C) but stressors such as pregnancy, birthing, lactating, and accelerated growth can render natural antibiotic production inadequate for counteracting the increased ROS concentration. An increased ROS concentration can result from the host's reduced ability to produce antioxidants, a higher accumulation of ROS from natural bodily functions, a higher accumulation of ROS from environmental factors, a higher accumulation of ROS from increased host accumulation susceptibility, and combinations thereof.

Animals are commonly administered antioxidants to counteract ROS and reduce oxidative stress, but excessive oxidative stress can diminish the efficacy of many antioxidants or create a threshold ROS level above which andioxidants are no longer effective. For example, metabolic insufficiency in an animal can prevent vitamin E or other antioxidants available in tissue and blood from counteracting ROS.

Essential oil compositions as described herein can provide antioxidant properties to a host system and generally reduce oxidative stress in animals. Essential oil compositions provided herein have high oxygen radical absorbance capacity (ORAC), which is the ability of a compound or composition to act as a proton donor and reducing agent for oxygen radicals. While many antioxidants are only effective against single ROS, the essential oil compositions provided herein have high ORAC against peroxyl radicals, hydroxyl radicals, peroxynitrite, superoxide anions, and singlet oxygen, among others. Moreover, essential oil compositions provided herein comprise both lipophilic and hydrophilic characteristics which provide complete cellular protection against ROS. For example, essential oil compositions provided herein can neutralize ROS both in cytoplasm and cell walls.

The essential oil compositions as provided herein can further be used as analogous or preferable substitutes for many commercial products used today, such as coccidiostats, subtherapeutic antibiotics, growth hormones, and other similar products. As such, a financial gain is realized by those selling milk, eggs, and meat products from animals consuming the compositions provided as the products can be more readily sold as "Natural", "Organic", "hormone-free", and/or "Antibiotic-Free".

Essential oil compositions as provided herein contain essential oils derived from plants (i.e., "natural" essential oils) and additionally or alternatively their synthetic analogues. Many embodiments comprise a combination of essential oils. Some embodiments comprise a combination of natural and synthetic essential oils. In some embodiments, synthetic essential oils can be a "nature's equivalent" synthetic blend, which generally mimics an essential oil assay of a natural essential oil by including at least 5, at least 10, at least 15, or at least 20 of the most critical essential oils within a natural essential oil. A critical essential oil can be determined by weight percent, and/or by pharmacological efficacy. For example, a nature's equivalent synthetic oil can comprise the following constitutions as provided in Table 1:

TABLE 1

Nature's Equivalent Synthetic Thyme Essential Oil:

| Constituent | Wt. % |
|---|---|
| Thymol | 42.7-44.08 |
| para-Cymene | 26.88-27.09 |
| Linalool | 4.3-4.34 |
| alpha-Pinene | 4.1-4.26 |
| alpha-Terpineol | 3.14-3.14 |
| 1,8-Cineole | 2.82-3.01 |
| beta-Caryophellene | 1.98-2.27 |
| Limonene | 1.59-1.78 |
| delta-3-Carene | 1.3-1.41 |
| beta-Myrcene | 1.26-1.31 |
| Linalyl Acetate | 1.11-1.24 |
| beta-Pinene | 1.04-1.22 |
| Terpinen-4-ol | 0.96-1.14 |
| alpha-Caryophyllene | 0.71-0.71 |
| gamma-Terpinene | 0.7-0.7 |
| Sabinene | 0.37-0.5 |
| Borneol | 0.27-0.32 |
| Camphene | 0.13-0.17 |

The disclosure herein indicates the efficacy of compositions comprising a plurality of essential oils which provide a synergistic effect beyond essential oils utilized in isolation. Further, essential oil compositions provided herein do not exhibit antagonistic effect between essential oil moieties within a composition. An essential oil composition generally includes an essential oil fraction and one or more additional components. The ratio of the essential oil fraction to the one or more additional components in a composition can depend on several factors such as administration method, and the nutritional/health needs and/or palate of a consuming subject, among others. In many embodiments, a consuming subject comprises an animal Compositions can comprise additional components including carriers, emulsifiers, and stabilizers, among others. Compositions as provided herein can be in the form of an emulsion.

The essential oils present in some embodiments can include oils from the classes of terpenes, terpenoids, phenylpropenes and combinations thereof. The essential oils present in some embodiments can include oils of plants from the Labiatae or Lamiaceae family, and the Lauraceae family, including hybrids of plants from one or both families. Suitable essential oils from the Lauraceae family can comprise those from the *Cinnamomum* genus. Within the *Cinnamomum* genus, suitable species can include *Cinnamomum burmannii, Cinnamomum cassia, Cinnamomum camphora, Cinnamomum loureiroi, Cinnamomum mercadoi, Cinnamomum oliveri, Cinnamomum osmophloeum, Cinnamomum ovalifolium, Cinnamomum parthenoxylon, Cinnamomum pedunculatum, Cinnamomum subavenium, Cinnamomum tamala, Cinnamomum verum, Cinnamomum verum*, and hybrids thereof.

Suitable essential oils from the Lamiaceae family can comprise those from one or more of the *Thymus* genus, the *Origanum* genus, the *Monarda* genus. Within the *Thymus* genus, a non-limiting list of suitable species can include *Thymus caespititius, Thymus capitatus, Thymus carnosus, Thymus citriodorus, Thymus glandulosus, Thymus Herba-borana, Thymus hyemalis, Thymus integer, Thymus pseudolanuginosus* (formerly *T. lanuginosus*), *Thymus mastichinia, Thymus montanus, Thymus moroderi, Thymus pannonicus, Thymus praecox, Thymus pulegioides, Thymus serpyllum, Thymus vulgaris, Thymus zygis*, and hybrids thereof. Within the *Origanum* genus, a non-limiting list of suitable species can include *Origanum amanum, Origanum compactum, cordifolium, Origanum dictamnus, Origanum laevigatum, Origanum libanoticum, Origanum majorana, Origanum microphyllum, Origanum onites, Origanum rotundifolium, Origanum scabrum, Origanum syriacum, Origanum vulgare*, and hybrids thereof. Within the *Monarda* genus, a non-limiting list of suitable species can include

*Monarda citriodora, Monarda clinopodioides, Monarda didyma, Monarda fistulosa, Monarda media, Monarda punctata*, and hybrids thereof.

The essential oils present in some embodiments can further include lavender essential oils from the *Lavandula* genus, Mexican bay leaf essential oils from the *Liteas* genus (e.g., *L. glaucescens*), West Indian bay tree essential oils from the *Pimenta* genus (e.g., *P. racemosa*), Indonesian bay leaf essential oils from the *Syzygium* genus, bay laurel essential oils from the *Laurus* genus (e.g., *L. nobilis*), California bay laurel essential oils from the *Umbellularia* genus (e.g., *U. californica*), lemon grass essential oils from the *Cymbopogon* genus (e.g., *C. ambiguous, C. citratus, C. flexuosus, C. martini, C. nardus, C. schoenanthus*), spearmint and peppermint essential oils from the *Mentha* genus (e.g., *M. spicata, M. piperita*), rosemary essential oils from the *Rosmarinus* genus (e.g., *R. officinalis*), sage essential oils from the *Salvia* genus (e.g., *S. sclarea*), hybrids thereof, and combinations thereof.

In some embodiments, an essential oil composition can include an essential oil fraction comprising three essential oils from the Lauraceae family and/or the Lamiaceae family In some embodiments, an essential oil composition can include an essential oil fraction comprising cinnamon essential oil from the *Cinnamomum* genus, thyme essential oil from the *Thymus* genus, and oregano essential oil the *Origanum* genus. In some embodiments, an essential oil composition can include an essential oil fraction comprising synthetic cinnamaldehyde and thyme essential oils from the *Thymus* genus and oregano essential oil from the *Origanum* genus. In some embodiments, oregano essential oil can comprise carvacrol. Additionally or alternatively, thyme essential oil can comprise thymol.

In some embodiments, the essential oil fraction can comprise about 1% to about 49.5% oregano essential oil, about 1% to about 49.5% thyme essential oil, and about 1% to about 49.5% cinnamon essential oil. In other embodiments, the essential oil fraction can comprise about 5% to about 47.5% oregano essential oil, about 5% to about 47.5% thyme essential oil, and about 5% to about 47.5% cinnamon essential oil. In other embodiments, the essential oil fraction can comprise about 10% to about 45% oregano essential oil, about 10% to about 45% thyme essential oil, and about 10% to about 45% cinnamon essential oil. In other embodiments, the essential oil fraction can comprise about 15% to about 42.5% oregano essential oil, about 15% to about 42.5% thyme essential oil, and about 15% to about 42.5% cinnamon essential oil. In other embodiments, the essential oil fraction can comprise about 20% to about 40% oregano essential oil, about 20% to about 40% thyme essential oil, and about 20% to about 40% cinnamon essential oil. In other embodiments, the essential oil fraction can comprise about 25% to about 37.5% oregano essential oil, about 25% to about 37.5% thyme essential oil, and about 25% to about 37.5% cinnamon essential oil. In other embodiments, the essential oil fraction can comprise about 30% to about 35% oregano essential oil, about 30% to about 35% thyme essential oil, and about 30% to about 35% cinnamon essential oil. In other embodiments, the essential oil fraction can comprise about 33.33% oregano essential oil, about 33.33% thyme essential oil, and about 33.33% cinnamon essential oil.

Many essential oil compositions comprise an essential oil fraction comprising an effective amount of carvacrol, an effective amount of thymol, and an effective amount of cinnamaldehyde. In an essential oil composition including an essential oil fraction comprising oregano essential oil, thyme essential oil, and cinnamon essential oil, the essential oil fraction can comprise three or more natural essential oils wherein the combined essential oils comprise at least an effective amount of carvacrol, at least an effective amount of thymol, and at least an effective amount of cinnamaldehyde. Suitable essential oils can include essential oils from the *Cinnamomum* genus, essential oils from the *Origanum* genus, essential oils from the *Thymus* genus, essential oils from the *Monarda* genus (e.g., *M. citriodora, M. clinopodioides, M. didyma, M. fistulosa, M. media, M. punctata*), essential oils from the *Trachyspermum* genus (e.g., *T. ammi*), essential oils from the *Nigella* genus (e.g., *N. sativa*), and combinations thereof. Other essential oils can be used such that effective amounts of carvacrol, thymol, and cinnamaldehyde are achieved in the essential oil fraction.

In an essential oil composition including an essential oil fraction comprising oregano essential oil, thyme essential oil, and synthetic cinnamaldehyde, the essential oil fraction can comprise two or more natural essential oils and synthetic cinnamaldehyde, wherein the combined essential oils and synthetic cinnamaldehyde comprise at an effective amount of carvacrol, at least an effective amount of thymol, and at least an effective amount of cinnamaldehyde. Suitable essential oils can include essential oils from the *Cinnamomum* genus, essential oils from the *Origanum* genus, essential oils from the *Thymus* genus, essential oils from the *Monarda* genus (e.g., *M. didyma*, and *M. fistulosa*), essential oils from the *Trachyspermum* genus (e.g., *T. ammi*), essential oils from the *Nigella* genus (e.g., *N. sativa*), and combinations thereof. Still other natural essential oils can be used such that effective amounts of carvacrol, thymol, and cinnamaldehyde are achieved in the essential oil fraction.

Some essential oil compositions comprise an essential oil fraction comprising an effective amount of carvacrol, an effective amount of thymol, and an effective amount of cinnamaldehyde. An effective amount of carvacrol can comprise at least about 10 wt. %, at least about 15 wt. %, at least about 20 wt. %, at least about 25 wt. %, at least about 30 wt. %, or at least about 33 wt. % of the essential oil fraction. An effective amount of thymol can comprise at least about 10 wt. %, at least about 15 wt. %, at least about 20 wt. %, at least about 25 wt. %, at least about 30 wt. %, or at least about 33 wt. % of the essential oil fraction. An effective amount of cinnamaldehyde can comprise at least about 10 wt. %, at least about 15 wt. %, at least about 20 wt. %, at least about 25 wt. %, at least about 30 wt. %, or at least about 33 wt. % of the essential oil fraction. In some embodiments, oregano essential oil can be replaced by one or more oils which include at least 45 wt. % carvacrol, at least 55 wt. % carvacrol, at least 65 wt. % carvacrol, or at least 75 wt. % carvacrol. In some embodiments, thyme essential oil can be replaced by one or more oils which include at least 30 wt. % thymol, at least 35 wt. % thymol, at least 40 wt. % thymol, or at least 45 wt. % thymol. In some embodiments, cinnamon essential oil can be replaced by one or more oils which include at least 35 wt. % cinnamaldehyde, at least 40 wt. % cinnamaldehyde, at least 50 wt. % cinnamaldehyde, or at least 75 wt. % cinnamaldehyde. Suitable sources of effective amounts of carvacrol, thymol, and/or cinnamaldehyde can include natural essential oils and/or synthetic essential oils.

Essential oil compositions can further comprise one or more of an effective amount of paracymene, an effective amount of eugenol, or an effective amount of citronella. An effective amount of paracymene can comprise at least about 5 wt. %, at least about 7.5 wt. %, at least about 10 wt. %, or at least about 12.5 wt. % of the essential oil fraction. An effective amount of eugenol can comprise at least about 5 wt. %, at least about 7.5 wt. %, at least about 10 wt. %, or at least about 12.5 wt. % of the essential oil fraction. An effective amount of citronella can comprise at least about 5 wt. %, at least about 7.5 wt. %, at least about 10 wt. %, or at least about 12.5 wt. % of the essential oil fraction.

In some embodiments, the essential oil fraction comprises 100% of the essential oil composition. An essential oil composition can further comprise a carrier. Carriers are ideally inert materials which do not react with the active components (i.e., the essential oil fraction) of the composition chemically, or bind the active components physically by adsorption or absorption. Liquid carriers include water, pure water, such as reverse osmosis water, milk, milk replacers, natural and/or commercial liquid feeds, or other liquids germane to animal dietary needs. Milk replacers can be formulated to generally mimic the content of milk. For example, a milk replacer can have a composition similar to that shown in Table 2:

TABLE 2

| Example Milk Replacer Formula | |
|---|---|
| Crude Protein, minimum | 22.50% |
| Lysine, minimum | 1.60% |
| Crude Fat, minimum | 16.50% |
| Crude Fiber, maximum | 0.50% |
| Calcium, minimum | 0.65% |
| Calcium, maximum | 1.15% |
| Phosphorus, minimum | 0.60% |
| Sodium, minimum | 0.50% |
| Sodium, maximum | 1.00% |
| Selenium, minimum | 0.25 ppm |
| Zinc, minimum | 50 ppm |

The composition can be at least about 50% liquid carrier by weight, at least about 75% liquid carrier by weight, at least about 85% liquid carrier by weight, or at least about 90% liquid carrier. In some embodiments, the composition will be about 80% to about 99% liquid carrier, about 85% to about 98% liquid carrier, about 90% to about 95% liquid carrier, or about 91% to about 94% liquid carrier. In other embodiments, the composition can be about 60% liquid carrier to about 74% liquid carrier, about 63% liquid carrier to about 71% liquid carrier, about 66% liquid carrier to about 68% liquid carrier, or about 67% liquid carrier.

Solid carriers can include limestone, diatomaceous earth, and animal feed. Carriers such as limestone, diatomaceous earth, and the like, are useful pre-feed carriers in that they may be first combined with an essential oil fraction to facilitate transportation and/or subsequent combination of the essential oil composition with a dry carrier such as animal feed. Animal feed can include hay, straw, corn husks, wheat, oats, barley, seeds, commercial livestock feed, and the like. In some embodiments where an essential oil composition comprises an essential oil fraction and a pre-feed carrier, the ratio of pre-feed carrier to the essential oil fraction can be at least 10:1, at least 15:1, at least 17:1, at least 18:1, or at least 20:1. In some embodiments, where an essential oil composition comprises an essential oil fraction and a carrier, with or without a pre-feed carrier, the ratio of carrier to the essential oil fraction can be at least about 1,000:1, at least about 4,500:1, at least about 9,000:1, at least about 20,000:1, at least about 35,000:1, or at least about 50,000:1.

The total amount of carrier in a composition can be determined based on the dietary needs of an animal, the tolerance of an animal to essential oil fraction, and other factors. Tolerance can include one or more of an animal's palatability and gastrointestinal tolerance to an essential oil fraction.

An essential oil composition can further comprise one or more emulsifiers. An emulsified essential oil fraction can increase the efficacy of an essential oil composition when ingested by a subject, and can make essential oil compositions more palatable to animals which consume the compositions orally. An essential oil fraction can be combined with an emulsifier and a dry carrier, or alternatively an essential oil fraction can be combined with an emulsifier and a liquid carrier, as disclosed above, to form an emulsion. The emulsifier can be combined with an essential oil fraction in a ratio of about 3:1 to about 1:3, about 2:1 to about 1:2, about 1.5:1 to about 1:1.5, or about 1:1. An essential oil composition comprising an essential oil fraction, a liquid carrier, and an emulsifier can have an average essential oil droplet size of less than about 25 microns, less than about 15 microns, less than about 10 microns, less than about 7.5 microns, or less than about 5 microns. In some embodiments, the average droplet size is less than about 7 microns, less than about 6 microns, less than about 5 microns, less than about 4 microns, or less than about 3 microns. As used herein, "droplet size" refers to the average size of an essential oil droplet within an emulsion.

An emulsifier combined with a liquid carrier can generally be referred to as a liquid emulsifier. In some embodiments, an emulsion can comprise up to about 35%, up to about 40%, up to about 45%, or up to about 50% essential oil fraction and emulsifier, with the balance comprising a liquid carrier. In some embodiments, an emulsion can comprise less than about 20%, less than about 15%, less than about 10%, about 5%, or less than about 5% essential oil fraction and emulsifier, with the balance comprising a liquid carrier. In some embodiments, an emulsion can comprise about 40% to about 60%, or about 45% to about 55% essential oil fraction and emulsifier, with the balance comprising a liquid carrier. In some embodiments, an emulsion can comprise about 1% to about 10%, about 2.5% to about 7.5%, or about 5% essential oil fraction and emulsifier, with the balance comprising a liquid carrier. In many embodiments the liquid carrier is water. The liquid carrier content can vary depending on the amount and type of emulsifier.

One or more emulsifiers can be used to form an emulsion. In some embodiments, one or more emulsifiers can additionally or alternatively be used as a stabilizer. Stabilizers can be used to alter the viscosity of an emulsion. Altering a viscosity can include maintaining a viscosity, increasing a viscosity, or decreasing a viscosity. A suitable emulsifier can be an emulsifier capable of achieving a threshold droplet size. In some embodiments a suitable emulsifier can achieve a suitable emulsion droplet size of less than about 25 microns, less than about 15 microns, less than about 10 microns, less than about 7.5 microns, or less than about 5 microns. In other embodiments, a suitable emulsifier can achieve a suitable emulsion droplet size of less than about 7 microns, less than about 6 microns, less than about 5 microns, less than about 4 microns, or less than about 3 microns. An emulsion having a droplet size below a suitable threshold enhances the efficacy of an essential oil composition.

A suitable emulsifier is larch arabinogalactan. Arabinogalactan generally comprises arabinose and galactose monosaccharides, and can be synthetic or natural. Natural arabinogalactan can be derived from plants or microbes. For example, arabinogalactan can be derived from larch trees, and many fruits, vegetables, and beans. In some embodiments, arabinogalactan is a preferred emulsifier because it is capable of achieving a desired droplet size and also acts as an antioxidant against many ROS, including peroxyl radicals, hydroxyl radicals, peroxynitrite, superoxide anions, and singlet oxygen. Accordingly, the hydrophilic characteristics of arabinogalactan enhance the cellular coverage of an essential oil composition. A particular type of arabinogalactan is larch arabinogalactan. Other suitable emulsifiers include polydextrose, chitin, psyllium, methyl-cellulose, hydrolyzed guar, guar, soy polysaccharide, oat bran, pectin, inulin, Fructooligosaccharides (FOS), xanthan gum, alginate, chemically modified cellulosic, Acacia, and gum Arabic.

In some embodiments, a suitable emulsifier can include a tannin compound, such as tannic acid. Tannin can be used as an alternative to or in combination with the emulsifiers described above. In some embodiments, a liquid emulsifier can comprise about 100% tannic acid, about 80% to about 95% tannic acid, about 60% to about 85% tannic acid, about 40% to about 60% or about 1% to about 50% tannic acid, with the balance being a liquid carrier.

An essential oil composition can further comprise one or more dedusting agents. Dedusting agents can comprise vegetable oil, olive oil, mineral oil and the like. The amount of dedusting agent in an essential oil composition can be determined based on the amount required to keep dust low while also allowing a dry composition to be "free flowing". A suitable "free flowing" characteristic can be determined by a funnel flow test or free flow test. A dedusting agent can be included in a feed in an amount between about 5-40 lbs/ton.

FIG. 1, illustrates a block flow diagram of a method 100 of making an essential oil composition, such as an essential oil emulsification in an aqueous carrier, is shown, according to some embodiments. One or more liquid emulsifiers are agitated 102. The one or more liquid emulsifiers are contacted 104 with one or more essential oils, sufficient to create an emulsion. The emulsion is agitated 106 while monitoring at least an emulsion temperature.

The liquid emulsifier (i.e., water and one or more emulsifiers) is agitated 102 in a vessel, such as by stirring, for a time sufficient to produce visible motion on the surface of the one or more liquid emulsifiers. The visible motion can be from the approximate surface center to one or more surface edges, at the perimeter of the vessel, for example. The time taken to reach such visible motion depends on the type of liquid emulsifier and ratio of emulsifier to water (e.g., viscosity). Once a suitable motion is established at the surface of the liquid emulsifier, one or more essential oils are added (e.g., contacted 104). The agitation of the liquid continues and an emulsion begins to form on contact. The contact rate or addition rate should be slow enough to substantially prevent volatilization of the essential oils.

The agitation continues during the addition of the essential oils. The emulsion begins to form assuming the rate of essential oil addition is slow enough to prevent a high shear environment, adversely affecting the volatilization of the oils. Agitation 106 of the emulsion then continues until the emulsion temperature reaches about 100° F. to about 110° F., about 103° F. to about 108° F. or about 104° F. to about 107° F. As the emulsion forms, the viscosity increases. The method of agitation should be adjusted to compensate for the increase in viscosity. For example, if a stirring method is used, the stirrer or paddle should increase in force to maintain the same level of movement of the liquid as the emulsion thickens.

The final emulsion can have an average droplet size of less than about 25 microns, less than about 15 microns, less than about 10 microns or less than about 5 microns. The smaller droplet size allows for a more stable emulsion and one that previously could not be utilized for animal health or agricultural uses due to instability and high volatilization rates.

Figure 2:
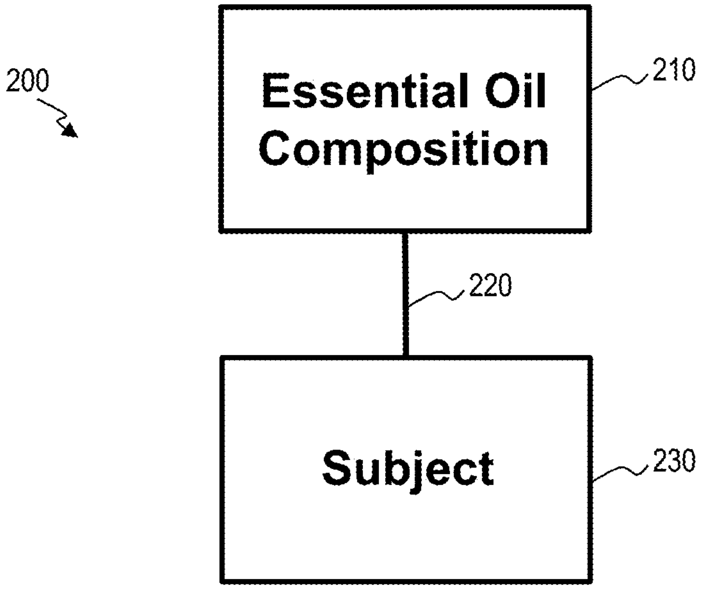
FIG. 2 illustrates a block flow diagram of a method of treating a subject with an essential oil treatment composition, according to one or more embodiments.

FIG. 2 illustrates a method 200 of treating a subject 230 to improve the health and/or feed efficiency of the subject, wherein the method comprises administering 220 an essential oil composition 210 to a subject. Administering 220 can include oral ingestion of the essential oil composition 210 as a feed or liquid, ingesting the essential oil composition in an encapsulated form, or applying the essential oil composition 210 topically. Pill-based or encapsulated administrations can be ideal for compositions which are not sufficiently palatable or an animal. However, administration via water or food-based carriers can be preferred for ease of administration.

A subject 230 can include all manner of animals, including poultry, horses, cows, pigs, and the like. Additionally or alternatively, subject 230 can include humans Additionally or alternatively, subject 230 can include fish, shrimp, crustaceans, and other aquaculture. Additionally or alternatively, subject 230 can include oviparous and ovuliparous animals The amount of essential oil composition administered to a subject 230 can depend on the species of the subject 230, the size of the subject 10, and the health status of a subject 230. For example, essential oil compositions can be administered regularly (i.e., daily) as a routine nutritional and health supplement, as an intervention (i.e., for several days or for the duration of a particular episode) in response to or in conjunction with increased stress, disease, birth, or other factors, or as a one-time administration during birth or a severe infection, disease, or injury. In some embodiments, essential oil compositions 210 can be administered 220 to a subject 230 as a routine feed, in a dose of about 0.1 mg of essential oil fraction to about 10 mg of essential oil fraction per kg of subject body weight (mg/kg), about 0.25 mg/kg to about 1.1 mg/kg, about 0.5 mg/kg to about 0.75 mg/kg, or about 0.5 mg/kg. Routine feed can include water, liquid feed, and solid feeds. Essential oil compositions 210 are generally administered in an amount above 5 ppm essential oil relative to the total feed dose, or approximately about 0.01 mg/kg. The dosage amount of essential oil can be varied based on the health of a subject 230. For example, an amount of essential oil per does can be increased in response to a subject 230 showing a deterioration in health, or other physical characteristic.

In some embodiments, essential oil compositions 210 can be administered 220 to a subject 230 as an intervention in a dose of about 1.0 mg/kg to about 10 mg/kg, about 2 mg/kg to about 7 mg/kg, or about 3.5 mg/kg. In some embodiments, essential oil compositions 210 can be administered 220 to a subject 230 as a one-time administration in a dose of about 10 mg/kg to about 30 mg/kg, about 13 mg/kg of essential oil fraction to about 24 mg/kg, or about 17 mg/kg.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLE 1

Evaluation of Essential Oils in Broiler Diets

A trial was conducted to evaluate the effect of an essential oil composition in broiler chicken diets on growth performance, feed efficiency, and mortality. As used herein, "broiler" refers to chicken raised for meat. The birds were raised without stress or challenge imposed by the researchers (e.g., no heat street, no detectable pathogen or bacterial infections, no pathogens and parasites introduced into feed, no excessive overcrowding in pens) The trial was conducted with 6 replications for each of 3 levels of feed containing an essential oil composition (SO1, containing thyme essential oil, oregano essential oil, and cinnamaldehyde) tested against a positive control feed, Essential Oil Product C, containing thyme essential oil and oregano essential oil, and a full negative control feed containing no essential oil. The feed formulations were as follows:

1. Negative Control: pure feed (no essential oil)
2. Positive Control: 1.0 lbs. of Essential Oil Product C per 1 ton of feed
3. SO1 Low: 0.5 lbs. of SO1 per 1 ton of feed
4. SO1 Mid: 1.0 lbs. of SO1 per 1 ton of feed
5. SO1 High: 1.5 lbs. of SO1 per 1 ton of feed Essential Oil Product C, comprises 90 wt. % carrier (~74.5 wt. % limestone, 15% wt. % diatomaceous earth), 0.5% wt. % de-dusting agent, 2.5 wt. % RO water, 2.5 wt. % commercial product Larafeed solids (Larch tree arabinogalactan), and 5 wt. % essential oil. The essential oils fraction comprises 20% thyme oil and 80% oregano oil, with a total assay of about 60.4 wt. % carvacrol, about 10.8 wt. % thymol, about 9 wt. % para-cymene, about 18.9 wt. % other secondary thyme oil and oregano oil constituents. SO1 comprises about 90 wt. % carrier (74.5 wt. % limestone, 15% wt. % diatomaceous earth), 0.5% wt. % de-dusting agent (e.g., mineral oil), 2.5 wt. % RO water, 2.5 wt. % commercial product Larafeed solids (Larch tree arabinogalactan), and 5 wt. % essential oil. The essential oils fraction comprises 33.33 wt. % thyme oil, 33.33 wt. % oregano oil, and 33.33 wt. % synthetic cinnamaldehyde, with a total assay of about 23.8 wt. % carvacrol, about 16.4 wt. % thymol, about 11.2 wt. % para-cymene, about 33.3 wt. % cinnamaldehyde about 14.6 wt. % other secondary thyme oil and oregano oil constituents.

The trial was run over 42 days with 660 1-day-old Cobb 500 cockeral broilers. The birds were wing banded, weighed, and randomly allotted to pens in one of 7 boxes on the date of delivery. Each battery brooder had 4 levels with 4 pens per level. Each level measured 3 feet wide by 4 feet long by 2 feet tall, resulting in a density of 0.545 $ft^2$/bird. The feeding schedule was as follows:

Days 0-16: 1.50 lbs. of feed per chick
Days 17-26: 2.50 lbs. of feed per chick
Days 27-36: 4.00 lbs. of feed per chick
Days 37-42: 2.50 lbs. of feed per chick The trial was conducted in a randomized complete block design, and data was analyzed using PROC MIXED procedure of SAS. Least squares means were separated by Fisher's Least Significant Difference. Generally, if birds are not stressed during trials, very little difference will be observed between treatments, as to bird growth, feed intake, average daily gain, and other factors. It is worth noting, then, that even under the stress-free conditions of this trial, advantages of the SO1 formulations over the positive control (Essential Oil Product C) and negative control were still observed. Particularly, the results indicate a synergistic effect of the three-oil SO1 formulation as compared to the two-oil Essential Oil Product C formulation. Cobb data for anticipated performance of representative birds has been included to validate the trial design. Table 3 includes data for body weight, average daily gain, average daily feed intake, gain to feed, and feed to gain data for birds over the six week trial:

TABLE 3

| | Feed Treatment and Time | | | | | | |
|---|---|---|---|---|---|---|---|
| | Control | EOP-C 1.0 lb | SO1 0.5 lb | SO1 1.0 lb | SO1 1.5 lb | SEM | P - Value |
| Number of pens | 6 | 6 | 6 | 6 | 6 | | |
| Body Weights, g | | | | | | | |
| Initial | 43.6 | 43.5 | 43.4 | 43.7 | 43.7 | 13.69 | 0.96 |
| 1st Week | 161.5 | 161.1 | 162.8 | 162.0 | 163.2 | 13.69 | |
| 2nd Week | 463.0 | 463.7 | 472.3 | 467.6 | 466.9 | 13.69 | |
| 3rd Week | 970.2 | 966.8 | 972.3 | 968.1 | 966.2 | 13.69 | |
| 4th Week | 1604.0 | 1593.3 | 1597.6 | 1583.5 | 1581.9 | 13.69 | |
| 5th Week | 2273.0 | 2249.2 | 2271.9 | 2239.9 | 2224.5 | 13.69 | |
| 6th Week | 2959.81 | 2913.29 | 2950.29 | 2939.04 | 2910.61 | 13.69 | |
| Average | 1210.7 | 1198.7 | 1210.1 | 1200.6 | 1193.9 | 5.18 | 0.10 |
| ADG, g/d | | | | | | | |
| 1st Week | 16.58 | 16.73 | 16.80 | 16.83 | 17.16 | 1.71 | 0.93 |
| 2nd Week | 42.54 | 42.81 | 43.07 | 43.38 | 43.56 | 1.71 | |
| 3rd Week | 72.74 | 72.26 | 72.82 | 71.61 | 71.23 | 1.71 | |
| 4th Week | 91.08 | 89.53 | 89.52 | 88.72 | 88.45 | 1.71 | |
| 5th Week | 95.81 | 94.54 | 96.14 | 93.03 | 91.70 | 1.71 | |
| 6th Week | 98.19 | 94.60 | 97.83 | 100.52 | 98.45 | 1.71 | |
| Overall ADG | 69.49 | 68.41 | 69.36 | 69.01 | 68.42 | 0.70 | 0.72 |
| ADFI, g/d | | | | | | | |
| 1st Week | 29.89 | 29.61 | 30.06 | 28.57 | 28.71 | 3.18 | 0.81 |
| 2nd Week | 58.05 | 56.04 | 58.38 | 58.07 | 58.58 | 3.18 | |
| 3rd Week | 104.30 | 101.50 | 103.43 | 102.95 | 105.31 | 3.18 | |
| 4th Week | 152.50 | 144.24 | 151.35 | 149.43 | 151.76 | 3.18 | |
| 5th Week | 177.25 | 174.43 | 181.27 | 175.61 | 173.37 | 3.18 | |
| 6th Week | 188.66 | 191.80 | 201.64 | 195.30 | 200.38 | 3.18 | |
| Average | 118.44 | 116.27 | 121.02 | 118.32 | 119.68 | 1.30 | 0.15 |

TABLE 3-continued

| | Feed Treatment and Time | | | | | | |
|---|---|---|---|---|---|---|---|
| | Control | EOP-C 1.0 lb | SO1 0.5 lb | SO1 1.0 lb | SO1 1.5 lb | SEM | P - Value |
| Gain to feed | | | | | | | |
| 1st Week | 0.56 | 0.57 | 0.56 | 0.59 | 0.60 | 0.02 | 0.71 |
| 2nd Week | 0.73 | 0.77 | 0.74 | 0.75 | 0.74 | 0.02 | |
| 3rd Week | 0.70 | 0.71 | 0.70 | 0.70 | 0.68 | 0.02 | |
| 4th Week | 0.60 | 0.62 | 0.60 | 0.60 | 0.59 | 0.02 | |
| 5th Week | 0.54 | 0.54 | 0.53 | 0.53 | 0.53 | 0.02 | |
| 6th Week | 0.52 | 0.49 | 0.49 | 0.51 | 0.49 | 0.02 | |
| Average | 0.61 | 0.62 | 0.60 | 0.61 | 0.60 | 0.01 | 0.50 |
| Feed to gain | | | | | | | |
| 1st Week | 1.81 | 1.77 | 1.79 | 1.70 | 1.68 | 0.05 | 0.76 |
| 2nd Week | 1.37 | 1.31 | 1.36 | 1.34 | 1.35 | 0.05 | |
| 3rd Week | 1.44 | 1.41 | 1.42 | 1.44 | 1.48 | 0.05 | |
| 4th Week | 1.68 | 1.61 | 1.69 | 1.69 | 1.72 | 0.05 | |
| 5th Week | 1.85 | 1.85 | 1.89 | 1.89 | 1.90 | 0.05 | |
| 6th Week | 1.93 | 2.04 | 2.07 | 1.95 | 2.04 | 0.05 | |
| Average | 1.68 | 1.66 | 1.70 | 1.67 | 1.69 | 0.02 | 0.55 |

Figure 3A:
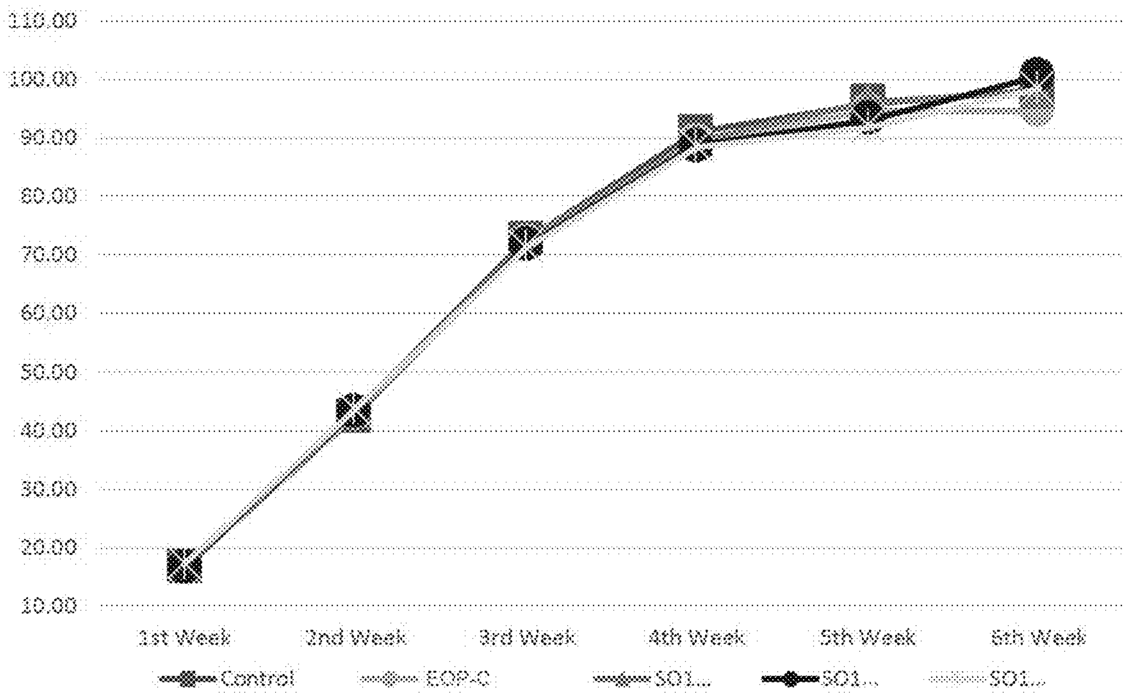
FIG. 3A illustrates average daily gain data for broilers, according to one or more embodiments.
Figure 3B:
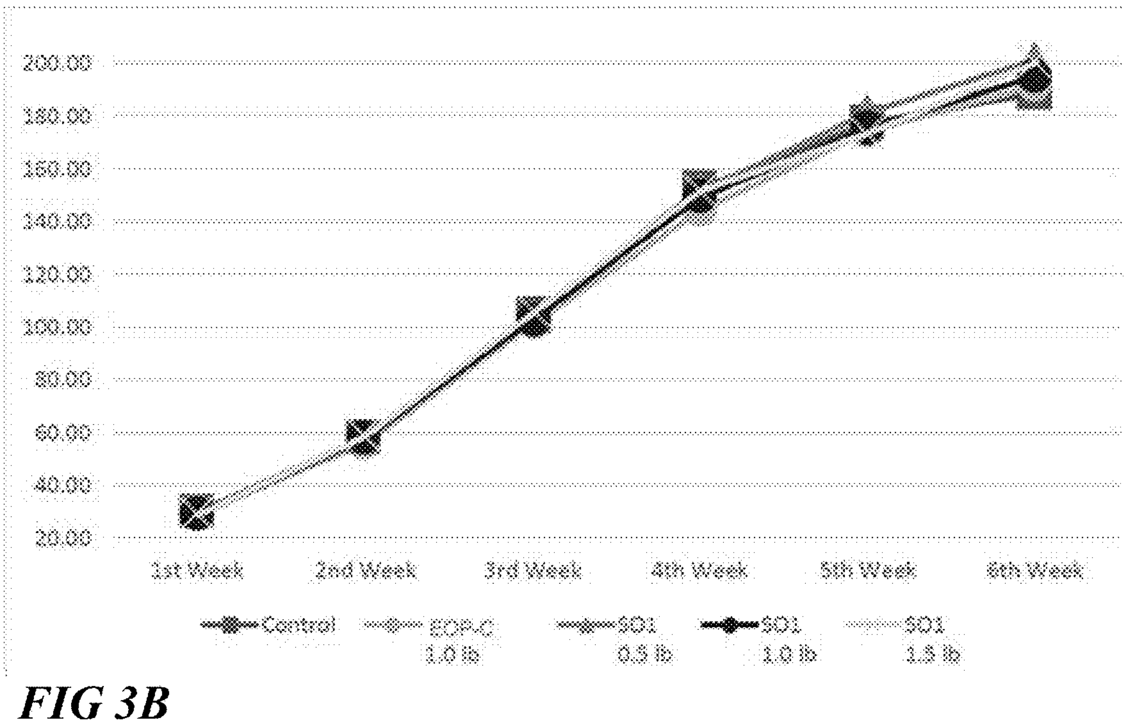
FIG. 3B illustrates average daily feed intake data for broilers, according to one or more embodiments.
Figure 3C:
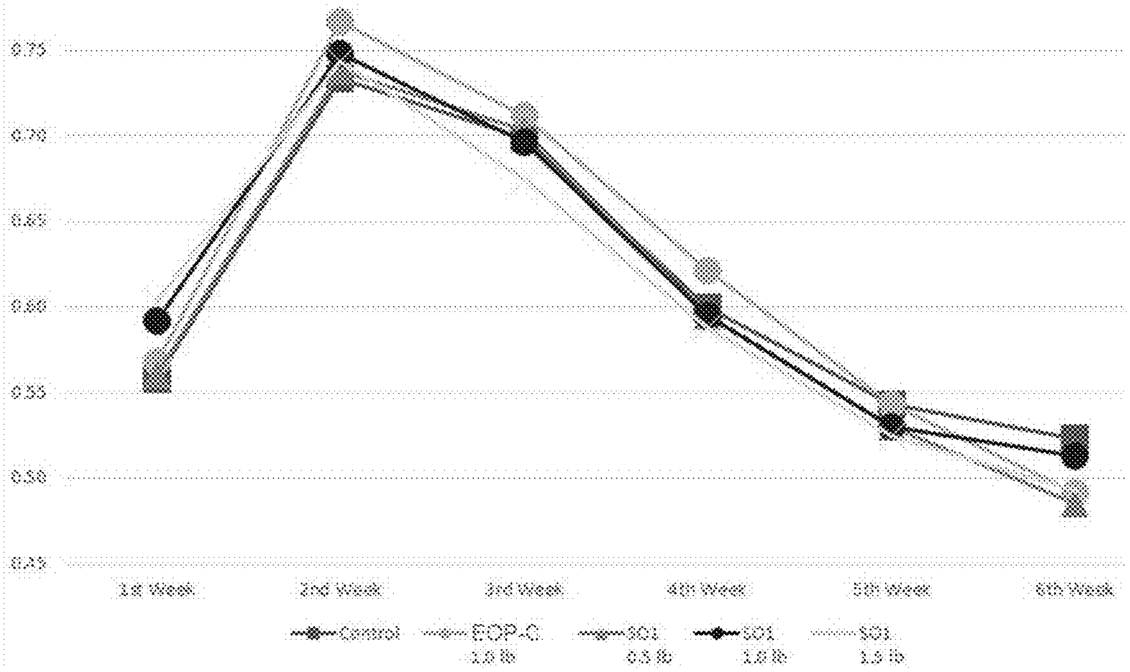
FIG. 3C illustrates gain to feed data for broilers, according to one or more embodiments.
Figure 4A:
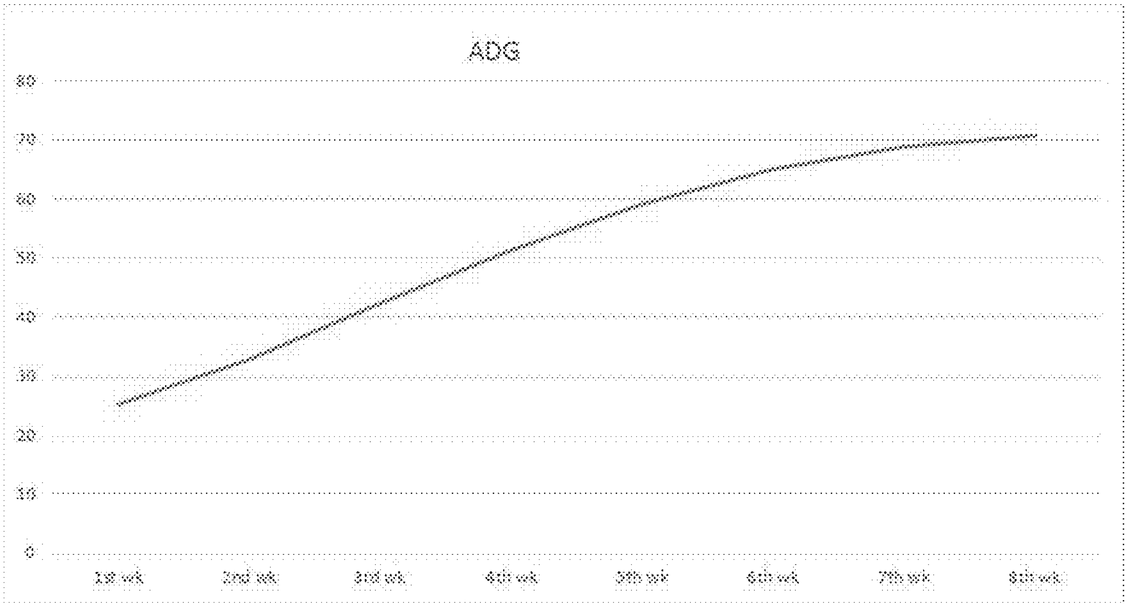
FIG. 4A illustrates Cobb anticipated average daily gain data for representative broilers, according to one or more embodiments.
Figure 4B:
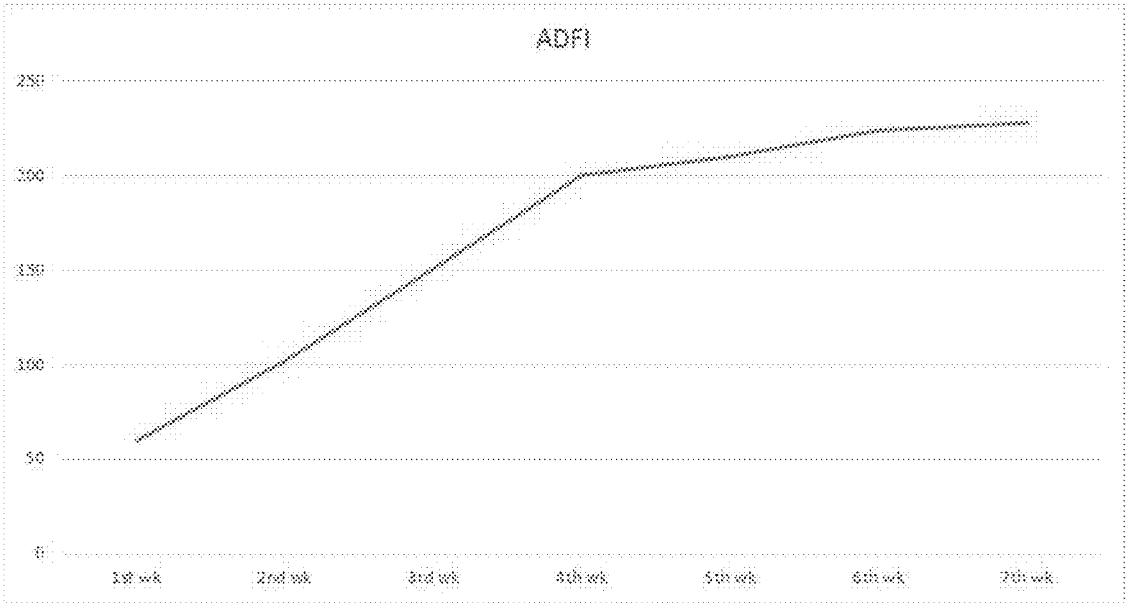
FIG. 4B illustrates Cobb anticipated average daily feed intake data for representative broilers, according to one or more embodiments.
Figure 4C:
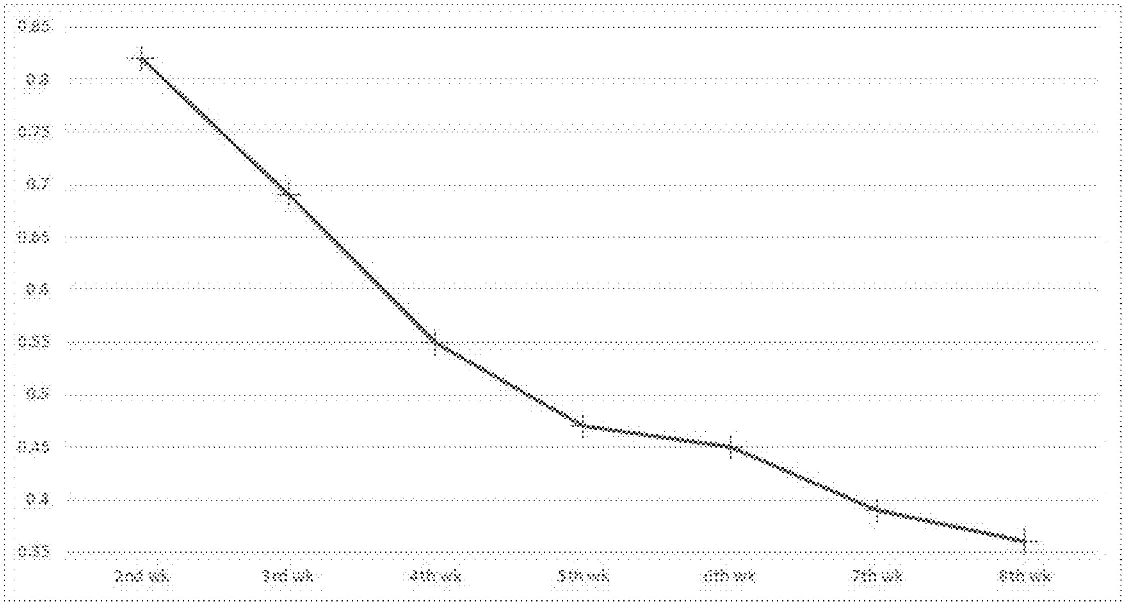
FIG. 4C illustrates Cobb anticipated gain to feed data for representative broilers, according to one or more embodiments.

FIG. 3A illustrates average daily gain data for broilers over the six trial weeks. Corresponding Cobb anticipated average daily gain data for representative broilers is illustrated in FIG. 4A. Birds fed the SO1 Mid formulation exhibited the highest average daily gain in week 6. FIG. 3B illustrates average daily feed intake data for broilers. Corresponding Cobb anticipated average daily feed intake data for representative broilers is illustrated in FIG. 4B. Birds fed the SO1 Low, Mid, and High formulations all exhibited higher daily feed intakes in week 6 than birds fed either the negative or positive control. FIG. 3C illustrates gain to feed data for broilers. Corresponding Cobb anticipated gain to feed data for representative broilers is illustrated in FIG. 4C.

It can be seen from FIG. 3A and Table 3 that the highest average daily gain was achieved in every week except week 4 by birds which were fed varying amounts of the SO1 formulation.

EXAMPLE 2

SO1 Diet Plan for Maximized Bird Health and Development

Strong development is critical in the early weeks of a bird's life, and accordingly a particularized feeding plan can be constructed to maximize bird health and development. Using average daily gain data from Table 3 above, the following feeding plan can be implemented under the experimental conditions described in Example 1:

1st Week: SO1 High

2nd Week: SO1 High

3rd Week: SO1 Low

4th Week: SO1 Low

5th Week: SO1 Low

6th Week: SO1 Mid

EXAMPLE 3

ORAC for Essential Oil Compositions

Table 4 illustrates the ORAC scores for oregano essential oil (*Origanum vulgare*), thyme essential oil (*Thymus vulgaris*), cinnamaldehyde, and ActiFibe (50 wt. % larch arabinogalactan, 50 wt. % water) against 5 of the most common detrimental ROS: peroxyl radicals ($RO_2$), hydroxyl radicals ($OH^{-1}$), peroxynitrate ($ONO2^{-1}$; $H_2O_2$+$NO_2^{-1}$), superoxide anion ($O_2^{-1}$), and singlet oxygen ($O_2$). Results are expressed as trolox equivalents (TE/100 g) for each composition:

TABLE 4

ORAC Capabilities of Essential Oil Compositions

| | Oxygen Radical Absorbance Capacity (TE/100 g) | | | | |
|---|---|---|---|---|---|
| Oxygen species | *Origanum vulgare* | *Thymus vulgaris* | Cinnamaldehyde | ActiFibe | *Origanum*, *Thymus*, Cinnamaldehyde, and ActiFibe Blend |
| Peroxyl radical | 510,800 | 386,000 | 18,800 | 20,600 | 325,800 |
| Hydroxyl radical | 1,046,900 | 896,700 | 49,300 | 46,400 | 710,700 |
| Peroxynitrite | 5100 | 4,300 | 3,500 | 1,200 | 5,500 |
| Superoxide anion | 0 | 0 | 978,900 | 16,600 | 342,900 |
| Singlet oxygen | 361,400 | 207,900 | 90,800 | 11,600 | 231,600 |
| Total ORAC | 1,924,200 | 1,494,900 | 1,141,300 | 96,400 | 1,616,500 |

Table 4 illustrates that a three oil blend with ActiFibe provides high ORAC for all five ROS.

EXAMPLE 4

3-Oil Screening Trial 640 1-day-old Cobb 500 cockerels were wing banded, weighed and randomly assigned to pens on the day of delivery. Each pen was 3 feet wide by 2 feet long by 2 feet tall holding 10 birds each; density was 0.6 sq. ft. per bird. The pens were contained within two battery cages in a single barn, each with battery cage having 4 levels and 8 pens per level for a total of 32 pens per battery. The experimental period was 35 days divided into three (3) feeding stages, starter, grower and finisher. Bird weight, average daily gain (ADG), average daily feed intake (ADFI), feed to gain (FG) and Coccidiosis oocyte counts were determined at each period. This study was performed with a large number of treatments in order to screen a number of possible treatments for further future investigations. The treatments included (1) a negative control (no stress, no treatment); (2) positive control, no treatment with stress (bird stress induced by administering ten times the normal level of the Advent coccidiosis vaccine in gel on top of the feed, a typical experimental broiler chick stress); (3) SO1 (75% limestone, 15% diatomaceous earth, 5% Larafeed and 5% essential oil at equal parts oregano essential oil, thyme essential oil, and cinnamaldehyde) at 0.75 pounds per ton of feed plus the cocci stress; (4) Essential Oil Product A (75% limestone, 15% diatomaceous earth, 5% Larafeed and 5% essential oil at 66.6% thyme essential oil, and 33.3% cinnamaldehyde), a combination of thyme and cinnamon oils, with the cocci stress, administered at 0.75 pounds per ton of complete feed; (5) artificial cinnamaldehyde, with the Advent vaccine cocci stress, administered at 0.75 pounds per ton; (6) Essential Oil Product B (60% Essential Oil Product C and 40% Larafeed), administered at 1.33 pounds per ton, with the Advent vaccine cocci stress; (7) Essential Oil Product C, described above, in a step-down program administered at 0.9, 0.6 and 0.4 pounds per ton in the starter, grower and finisher phases, respectively.

Average bird weights for these nine (9) treatments, from lowest to highest at thirty-five (35) days were: (a) Positive control at 1984.0 grams, as might be expected; (b) Negative control at 2039.9 grams; (c) Essential Oil Product B at 2093.1 grams; (d) Essential Oil Product C at 2153.4 grams; (e) Essential Oil Product A at 2172.0 grams; (f) cinnamaldehyde at 2180.2 grams, and (g) SO1 at 2202.4 grams. In this trial the top two treatments in bird weight performance was SO1, the 3-oil blend of oregano, thyme and cinnamaldehyde and ActiFibe, the prebiotic fiber. The positive impact of this product on gut health and host immunity led to higher feed efficiency and weight gain of all other products.

The feed-to-gain ratio (F:G) results in this trial were in the range of 1.19 to 1.26 for the starter phase, between 2.89 and 3.66 for the grower phase and 0.98 to 1.09 for the finisher phase, with lower F:G values being preferred. The 3-oil blend SO1 treatment resulted in the lowest F:G value in the starter phase at 1.19, the grower phase at 2.89, and just slightly above the lowest F:G value, 0.98, in the finisher phase at 1.00. Therefore birds that received the SO1 3-oil treatment not only grew the most, but were the most efficient in feed conversion of all the treatments in two of the three phases and next to best in the third phase. More specifically, the combination of the three oils in feed resulted in broiler birds gaining more weight and doing it more efficiently than the other two oil essential oil combinations. The SO1-treated birds also had the lowest mortality of all treatment groups.

EXAMPLE 5

3-Oil Titration Study 640 1-day-old Cobb 500 cockerels were wing banded, weighed and randomly assigned to pens on the day of delivery. Each pen was 3 feet wide by 2 feet long by 2 feet tall holding 10 birds each; density was 0.6 sq. ft. per bird. The pens were contained within two battery cages in a single barn, each with battery cage having 4 levels and 8 pens per level for a total of 32 pens per battery. The experimental period was 42 days divided into four feeding stages: starter, grower, finisher and withdrawal. Bird weight, average daily gain (ADG), average daily feed intake (ADFI) and gain to feed (G:F) were determined at each period. This study was performed with four treatments: three levels of SO1 against Essential Oil Product C, a two oil product, described above. This was not a challenge study, and therefore the broiler birds were not under any particular health or disease stress. The results showed that lower essential oil levels for SO1 performed the best; average treatment bird weights at day 42 were 2950.3 grams for SO1 at 0.5 pounds per ton of complete feed, 2939.0 grams at 1.0 pound per ton SO1 and 2910.6 grams at 1.5 pounds per ton SO1. This is a typical animal response to essential oils where titrations must be done to determine the best response level for the host in the environment that they are in. Birds administered Essential Oil Product C at 1 pound per ton complete feed showed an average bird weight at 42 days of 2913.3 grams, a lower weight compared to the 2950.3 grams for birds fed SO1 at 0.5 pounds per ton of complete feed. These results show that not only did the three-oil blend outperform the two oil blend, but less 3-oil blend was required in order to achieve a superior result.

EXAMPLE 5

3-Oil Blend Challenge Against Commercial Products and Industry Standard Treatments 640 1-day-old Cobb 500 cockerels were wing banded, weighed and randomly assigned to pens on the day of delivery. Each pen was 3 feet wide by 2 feet long by 2 feet tall holding 10 birds each; density was 0.6 sq. ft. per bird. The pens were contained within two battery cages in a single barn, each with battery cage having 4 levels and 8 pens per level for a total of 32 pens per battery. The experimental period was 42 days divided into four feeding stages: starter, grower, finisher and withdrawal. Bird weight, average daily gain (ADG), average daily feed intake (ADFI), feed to gain (FG) and Coccidiosis oocyte counts were determined at each period. This study was conducted with four treatments in order to compare Essential Oil Product C and SO1 in a challenge setting using Advent Coccidiosis vaccine at 10× the normal level, comparing it to a typical industry treatment protocol with Coban/BMD. The treatments were (1) a positive control, no treatment with stress (bird stress induced by administering ten times the normal level of the Advent coccidiosis vaccine in gel on top of the feed, a typical experimental broiler chick stress); (2) SO1 at 1.0 pounds per ton of feed plus the cocci stress; (3) an existing Ralco essential oil blend, Essential Oil Product C, as described above, with the cocci stress, administered at 1.0 pounds per ton of complete feed; and (4) a standard industry treatment protocol, the combination of Coban (Elanco Monensin), a drug used to prevent coccidiosis in chickens, turkey and quail with BMD (Zoetis), a type A Medicated Article for the prevention and control of necrotic enteritis, increased rate of weight gain and improved feed efficiency in poultry, all with the standard cocci vaccine stress with the drugs used at label directions.

Average treatment body weights of the birds at 42 days of age were: 2745.7 grams for the positive control; 2782.6 grams for SO1; 2766.1 grams for Essential Oil Product C, and 2777.8 grams for the Coban/BMD treatment. Feed-to-gain results, respectively, were 2.28, 2.45, 2.17 and 2.47. Hence, SO1 showed the greatest gain of all treatments, including the drug treatment, and further evidenced synergistic effects of the 3-oil blend.

EXAMPLE 5

Swine Finisher Trial 1248 standard cross-bred finishing pigs from about 135 pounds to about 245 pounds were allocated to one of four treatments: (1) control with standard finishing diet; (2) control diet supplemented with 0.75 pounds per ton Essential Oil Product C; (3) control diet supplemented with 0.50 pounds per ton SO1, and (4) SO1 at 0.75 pounds per ton in the control or standard finisher diet. The pigs were house in 48 pens total and balanced for gender. At the end of each of four (4) fourteen (14) day periods the pigs were weighed and feed consumption was tracked so that in total pig weights, average daily gain (ADG), average daily feed intake (ADFI) and FCR response could be determined.

Total average individual treatment weight gains per pig over the 42 day period were: 107.2 pounds per pig for the control group; 110.6 pounds per pig for the Essential Oil Product C group; 115.0 pounds per pig for the lower level SO1 group and; 112.0 pounds per pig in the upper inclusion level SO1 group. Overall average FCR Response for the treatments in the same order were: 3.19, 3.10, 3.01 and 3.13, respectively. The best weight gain was observed in the lower level SO1 treatment (0.50 pounds per ton of complete feed) and that treatment also had the best feed conversion at feed-to-gain of 3.01. While this was a "non-challenged" trial the pigs are in their normal finishing barn swine habitat and the superior results for SO1 demonstrated the efficacy of the 3-oil blend independent from animal species.

EXAMPLE 5

*Vibrio* in Shrimp

Several strains of the bacteria *Vibrio* are responsible for severe economic losses in commercial shrimp production worldwide. *Vibrio* causes acute hepatopancreas necrosis (AHPND) or early mortality syndrome (EMS). Antibiotics are beginning to lose efficacy against *Vibrio* and other aquaculture pathogens, in part due to an increased prevalences of resistant bacteria in the human food supply. Essential oils are here demonstrated to be an alternative to antibiotics in this application.

Three *Vibrio parahaemolyticus* strains isolated from shrimp in Mexico were used to test the efficacy of Essential Oil Product D (RO water 67.75%, Larafeed 12.75%, essential oil 18.5% and 1% TIC Gum, with the essential oil combination at 80:20 oregano oil:thyme oil) and SO1 essential oils to determine their minimum inhibitory concentrations (MIC) or the level at which the essential oils terminate the bacteria. VP 834, 276 and 696 MIC were determined using standard microbiological procedures including serial dilutions. VP 834 was isolated from shrimp stomach in Mexico, VP 276 was isolated from shrimp hepatopancreas in Mexico, and VP 696 was isolated from shrimp larva in Mexico. The results of that testing showed that the MIC of Essential Oil Product D and SO1 against 834, 276 and 696 were, in ppm, (117, 58), (234, 234) and (117, 58), respectively. Given the three strain test results, SO1 was more effective than Essential Oil Product D in two cases, and was equal to Essential Oil Product D in the other. This trial further demonstrates the synergistic benefits of the three oil blend over two oil blends.

What is claimed is:

1. A method of enhancing the health and feed efficiency of an animal, comprising:

orally administering an essential oil composition to an animal;

wherein the administering provides at least one of an enhanced feed efficiency, enhanced health, increased body weight, or increased weight gain rate of the animal, wherein the animal is at least one of poultry, horses, cows, or pigs, wherein the essential oil composition comprises:

an essential oil fraction comprising at least two essential oils selected from the group consisting of thyme essential oil, oregano essential oil, cinnamon essential oil, and combinations thereof, an emulsifier comprising larch arabinogalactan, and a solid carrier selected from the group consisting of limestone, diatomaceous earth, animal feed, and combinations thereof, wherein the emulsifier associates with the essential oil fraction to form an essential oil emulsion in which the average droplet size is about 10 microns or less, wherein a ratio by weight of the emulsifier to the essential oil fraction in the essential oil emulsion is about 3:1 to about 1:3, and wherein the essential oil emulsion is present in an amount of about 1 wt. % to about 60 wt. % based on the total weight of the essential oil composition.

2. The method of claim 1, wherein the oral administration comprises ingesting the essential oil composition in a solid feed form.

3. The method of claim 1, wherein one of the essential oils in the essential oil fraction is thyme essential oil and the thyme essential oil comprises oil derived from *Thymus caespititius, Thymus capitatus, Thymus carnosus, Thymus citriodorus, Thymus glandulosus, Thymus Herba-borana, Thymus hyemalis, Thymus integer, Thymus pseudolanuginosus, Thymus mastichinia, Thymus montanus, Thymus moroderi, Thymus pannonicus, Thymus praecox, Thymus pulegioides, Thymus serpyllum, Thymus vulgaris, Thymus zygis*, or combinations thereof.

4. The method of claim 1, wherein the essential oil fraction comprises oregano essential oil and thyme essential oil.

5. The method of claim 1, wherein one of the essential oils in the essential oil fraction is oregano essential oil and the oregano essential oil comprises oil derived from one or more of *Origanum amanum, Origanum compactum, Origanum cordifolium, Origanum dictamnus, Origanum laevigatum, Origanum libanoticum, Origanum majorana, Origanum microphyllum, Origanum onites, Origanum rotundifolium, Origanum scabrum, Origanum syriacum, Origanum vulgare*, or combinations thereof.

6. The method of claim 4, wherein the oregano essential oil comprises synthetic carvacrol or synthetic thymol.

7. The method of claim 1, wherein one of the essential oils in the essential oil fraction is cinnamon essential oil and the cinnamon essential oil comprises oil derived from one or more of *Cinnamomum burmannii, Cinnamomum cassia, Cinnamomum camphora, Cinnamomum loureiroi, Cinnamomum mercadoi, Cinnamomum oliveri, Cinnamomum osmophloeum, Cinnamomum ovalifolium, Cinnamomum parthenoxylon, Cinnamomum pedunculatum, Cinnamomum subavenium, Cinnamomum tamala, Cinnamomum verum*, and hybrids thereof.

8. The method of claim 1, wherein essential oil fraction comprises natural cinnamaldehyde or synthetic cinnamaldehyde.

9. The method of claim 1, wherein the essential oil composition further comprises at least one of lavender essential oil, Mexican bay leaf essential oil, West Indian bay tree essential oil, Indonesian bay leaf essential oil, bay laurel essential oil, California bay laurel essential oil, lemon grass essential oil, spearmint essential oil, peppermint essential oil, rosemary essential oil, sage essential oil, or combinations thereof.

10. The method of claim 1, wherein the essential oil emulsion is present in an amount of about 2.5 wt. % to about 60 wt. % based on the total weight of the essential oil composition.

11. The method of claim 1, wherein the essential oil composition does not comprise materials that bind the essential oil fraction physically by adsorption or absorption, other than the emulsifier.

12. The method of claim 1, wherein the solid carrier is present in an amount of at least about 40% by weight, based on a total weight of the essential oil composition.

13. The method of claim 1, wherein the administering further causes at least one of the following in the animal:

reduced or eliminated microbial infection, reduced or eliminated oxidative stress, reduced or eliminated infection or death during transport, enhanced egg characteristics, increased growth rate, reduced or eliminated birth mortality, increased or improved body score conditions, increased reproductive success, increased gut health maturation, or combinations thereof.

14. The method of claim 1, wherein the emulsifier further comprises at least one selected from the group consisting of polydextrose, chitin, psyllium, methylcellulose, hydrolyzed guar, guar, soy polysaccharide, oat bran, pectin, inulin, fructooligosaccharides, xanthan gum, alginate, chemically modified cellulose, gum arabic, and combinations thereof.

* * * * *